United States Patent

Galla et al.

Patent Number: 5,846,814
Date of Patent: Dec. 8, 1998

[54] SOLID-SUPPORTED MEMBRANE BIOSENSORS

[75] Inventors: Hans-Joachim Galla; Claudia Steinem, both of Münster; Karsten Reihs, Köln, all of Germany

[73] Assignee: Bayer Aktiengesllschaft, Leverkusen, Germany

[21] Appl. No.: 803,586

[22] Filed: Feb. 20, 1997

[30] Foreign Application Priority Data

Feb. 27, 1996 [DE] Germany .................. 196 07 279.4

[51] Int. Cl.$^6$ .................. C12M 1/34; G01N 33/553; G01N 27/26; A61B 5/103

[52] U.S. Cl. .................. 435/287.2; 435/287.1; 435/817; 436/525; 436/151; 436/806; 422/82.01; 427/2.11; 427/2.13; 204/403

[58] Field of Search .................. 204/403; 435/174, 435/4, 817, 287.1, 287.2; 436/806, 525, 527, 151; 427/211, 2.12, 2.13; 438/806; 422/82.02, 82.01

[56] References Cited

FOREIGN PATENT DOCUMENTS

| | | |
|---|---|---|
| 0 441 120 A2 | 8/1991 | European Pat. Off. . |
| WO 89/01159 | 2/1989 | WIPO . |
| WO 92/17788 | 10/1992 | WIPO . |
| WO 93/21528 | 10/1993 | WIPO . |
| WO 94/07593 | 4/1994 | WIPO . |

OTHER PUBLICATIONS

Lang et al, *A New Class of Thiolipids for the Attachment of Lipid Bilayers on Gold Surfaces,* American Chemical Society, Langmuir 1994, 10, 197–210.

Primary Examiner—Robert J. Warden
Assistant Examiner—Alexander Noguerola
Attorney, Agent, or Firm—Sprung Kramer Schaefer & Briscoe

[57] ABSTRACT

The new membrane biosensors consist of a solid A as a support, a lipid bilayer B as a membrane, spacers C incorporated between A and B and a receptor D embedded in the lipid bilayer. The new membrane biosensors are characterized in particular by their spacer C, which consists of a molecule of ethanolamine which forms an ester bond to the phosphatide group of the lipid bilayer B, an oligopeptide in helical or pleated sheet structure formed from 4–20 $C_2$–$C_{10}$-α-amino acids and a reactive group which enters into a chemical or physicochemical bond with the support A.

8 Claims, 4 Drawing Sheets

SOLID-SUPPORTED MEMBRANE BIOSENSORS

BACKGROUND OF THE INVENTION

The invention relates to new membrane biosensors which consist of a solid as a support, a lipid bilayer as a membrane, which is bonded to the solid via a spacer, and a receptor, which does not come into contact with the solid, in the lipid bilayer. In particular, the new membrane biosensors are characterized by their special spacers, which contain an oligopeptide in helical or pleated sheet structure.

Membrane biosensors of the fundamental structure described above can fulfil, inter alia, two objects:

ligands which have a specific biological interaction with the incorporated receptor can be detected as analytes in liquids of biological origin, wherefrom medical test rods or other medical or biological analysis methods can be developed; and various ligands in suitable solvents can be examined for their suitability for pair formation (specific interaction) with a prestated receptor, wherefrom, for example, the development of chemical/biological components for new active compounds in the field of pharmaceuticals and plant protection agents can be realized and specifically developed.

Receptors can only display the mentioned actions in biological systems when they are situated within a cell membrane. Such cell membranes in general consist of a lipid bilayer. For example, the binding of a ligand specific to the receptor present can effect an opening of the ion channel of this receptor, such that an electrical signal through the lipid bilayer into the interior of a biological cell or from the interior of such a biological cell is possible. Synthetic membrane biosensors which are intended to be employed for the abovementioned analytical and other purposes must, however, be supported by a solid for better handleability and storability. A lipid bilayer attached thereto then means the readjustment of the cell membrane necessary for the embedding of the receptor. For ensuring the activity of the receptor, which in cells of biological origin reaches into the cell interior and only has contact there with the cell fluid, it is necessary to avoid contact of the receptor with the supporting solid.

To avoid contact of the supporting solid with the receptor, the lipid bilayer was therefore provided on the side facing the support with a spacer of polyoxyethylene (polyoxyalkylene) groups (EP 441 120-A; WO 93/21528; Langmuir 10 (1994), 197–210). Biosensors of the type mentioned, however, appear to be difficult to prepare and use in practice, as the polyoxyalkylene bridge members (spacers) in self-assembly (SA) processes did not result in adequately stable organization states, whereby use and reproducibility of the results were severely restricted.

SUMMARY OF THE INVENTION

It has now been found that the disadvantages mentioned can be overcome if oligopeptide-containing spacer groups are employed.

The invention relates to solid-supported membrane biosensors, consisting of a solid A as a support, a lipid bilayer B as a membrane with spacers C incorporated between A and B and a receptor D embedded in the lipid bilayer, where a) A on the surface facing D consists of a corrosion-resistant material which allows sensing of an electrical signal, b) the lower lipid monolayer of B consists to 1–40% of all lipid molecules of di-($C_8$–$C_{30}$-acyl)-phosphatidyl compounds with a naturally occurring head group and to 60–99% of a di-($C_8$–$C_{30}$-acyl)-phosphatide which, however, carries the spacer C instead of the head group, and whose upper lipid monolayer consists to 100% of di-($C_8$–$C_{30}$-acyl)-phosphatidyl compounds with a naturally occurring head group, all acyl groups of a layer essentially being of equal length, but the acyl groups of the lower lipid monolayer being of equal or different length to those of the upper lipid monolayer, c) C consists of 1 molecule of ethanolamine which forms an ester bond to the phosphate group of B, an oligopeptide in helical or pleated sheet structure formed from 4–20 $C_2$–$C_{10}$ -α-amino acids and a reactive group which enters into a chemical or physicochemical bond with A, all C of the biosensor being identical, and d) D has no contact with A.

The invention further relates to a process for the preparation of a solid-supported membrane biosensor, such as described above, which comprises either (1) applying a solution of 1 part of lipid provided with a spacer and 1–$10^6$ parts of non-spaced lipid in water, an organic solvent from the group consisting of $C_1$–$C_4$-alkanols and $C_3$–$C_6$-ketones or a mixture of several of them to a support A, a lower lipid monolayer, consisting of 60–99% of lipid molecules provided with the spacer and of 1–40% of non-spaced lipid molecules being spontaneously formed, (1a) the upper lipid monolayer additionally also being spontaneously formed from aqueous solutions, or (1b) in solutions not containing water only the lower lipid monolayer being formed, which after a washing process with the organic solvent used is completed to give the lipid bilayer by applying a solution of non-spaced lipid molecules in water, and transferring a micelle solution of a receptor suspension to the lipid bilayer formed according to (1a) or (1b), the receptor D being spontaneously arranged in the lipid bilayer, or (2) transferring a solution of lipid provided with a spacer in one of the above solvents to a support A, after formation of a submonolayer of the lipid removing this solution again from the support, rinsing the submonolayer formed on the support with one of the above solvents and then a micellar solution of water, non-spaced lipid, surfactant and transferring receptor D to the submonolayer, the lipid bilayer being spontaneously completed and the receptor D being spontaneously arranged in the lipid bilayer, or (3) applying a vesicle solution, consisting of receptor molecules and lipids, to the submonolayer formed on the support A, the vesicles spontaneously fusing to the submonolayer and the receptor D spontaneously arranging in the lipid bilayer.

BRIEF DESCRIPTION OF THE DRAWINGS

The attached FIG. 1 shows the construction with a support A, a lipid bilayer B, a spacer C bonding together A and B, and an embedded receptor D. FIG. 2 shows a non-spaced lipid molecule; FIG. 3 shows a spaced lipid molecule. FIGS. 4a to 4c show the stepwise construction of the membrane biosensor.

DETAILED DESCRIPTION OF THE INVENTION

Figure 1:
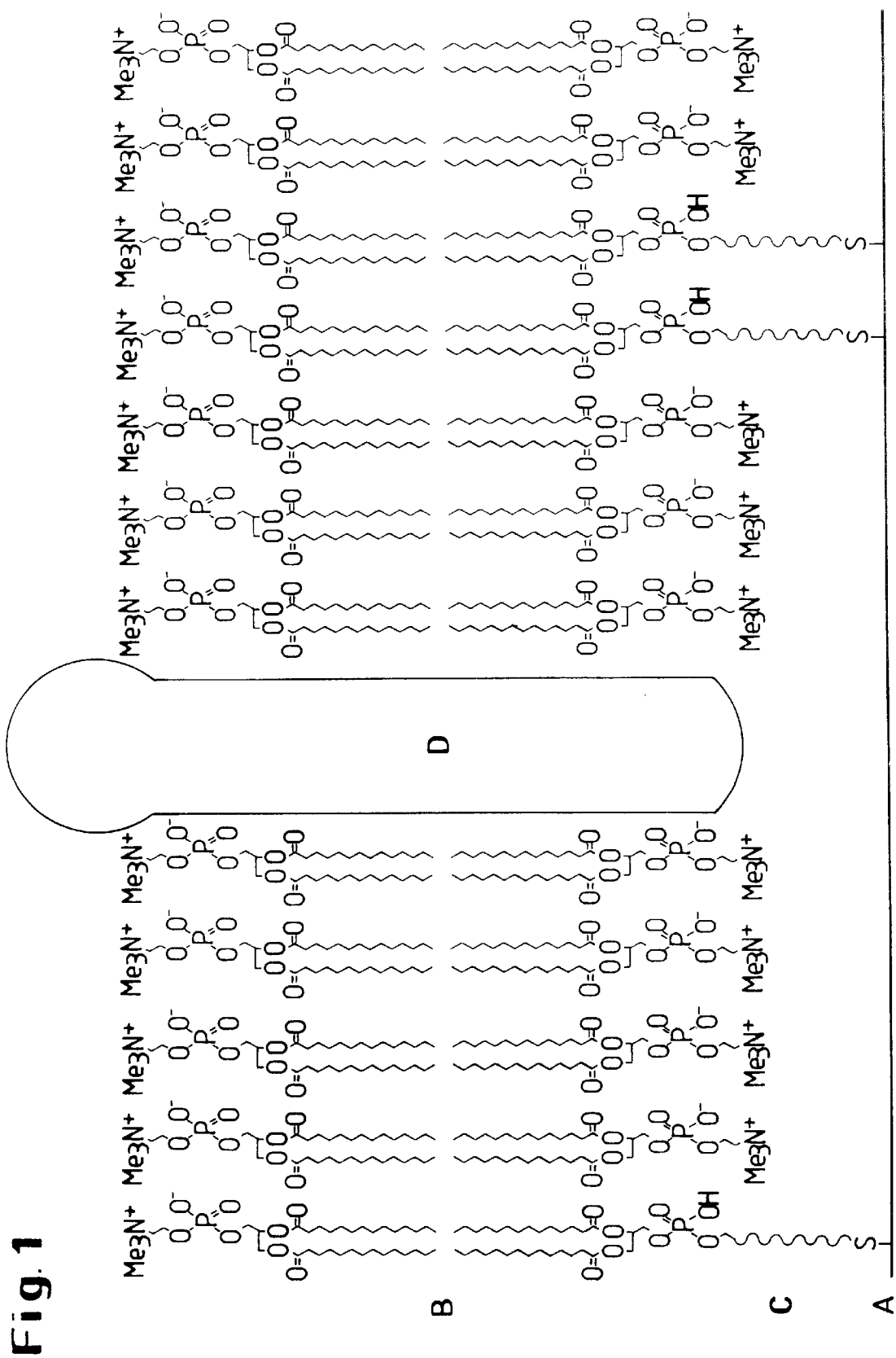
FIGS. 1, 2, 3 and 4a to 4c illustrate the inventive membrane bio-sensor. Thus.

Possible supports A are any desired dimensionally stable solids which can consist of a ceramic substance, a metal or a duroplastic or thermoplastic polymer which on the surface facing the receptor D consists of a corrosion-resistant material with sensing of an electrical signal. In the case in which the support consists of a corrosion-resistant metallic material, it does not need to be further modified or coated on its surface. This applies, for example, to (semi)noble metals such as gold, silver, platinum, palladium, rhodium, ruthenium, iridium or copper. If the support consists of a non-corrosion-resistant metal, it must be plated or coated in another way (e.g. wet chemically or electrolytically) on the surface facing D with one of the corrosion-resistant (semi) noble metals mentioned.

A corrosion-resistant support material which simultaneously makes possible the sensing of an electrical signal is furthermore doped silicon.

In the case of non-corrosion-resistant metallic materials or in the case of duroplastic or thermoplastic polymers, the surface which faces the receptor D must be plated or coated in another way by one of the corrosion-resistant (semi)noble metals mentioned.

On the support A is arranged a lipid bilayer B. This lipid bilayer consists of a large number of molecules of di-($C_8$–$C_{30}$-acyl)-phosphatidylcholine, which are aligned with the hydrocarbon ends of the acyl groups together and have a highly orientated structure. While the upper layer of this bilayer consists to 100% of such phosphatidylcholine molecules, the lower layer of the bilayer B is only constructed to 1–40% of all lipid molecules of di-($C_8$–$C_{30}$-acyl)-phosphatidylcholine and to 60–99% of a di-($C_8$–$C_{30}$-acyl)-phosphatide, in which there is a spacer C instead of the choline. In a preferred manner, the biosensors according to the invention consist in the lower lipid monolayer of B to 10–30% of all lipid molecules of di-($C_8$–$C_{30}$-acyl)-phosphatidylcholine and to 70–90% of a di-($C_8$–$C_{30}$-acyl)-phosphatide which, however, carries the spacer C instead of the choline, and in the upper layer to 100% of di-($C_8$–$C_{30}$-acyl)-phosphatidylcholine. In a furthermore preferred manner, the acyl groups contain 10–24 C atoms.

The two long-chain fatty acids whose acyl groups are esterified with the glycerol have, in the form of the acyl groups, 8–30 C atoms, preferably 10–24 C atoms. A typical acyl radical is the myristyl radical —CO—$(CH_2)_{12}$—$CH_3$ having a total of 14 C atoms. Other examples of acyl groups which are suitable according to the invention are the caprylyl radical —CO—$(CH_2)_6$—$CH_3$ having 8 C atoms, the capronyl radical —CO—$(CH_2)_8$—$CH_3$ having 10 C atoms, the lauryl radical, the palmityl radical, the stearyl radical, ($C_{20}$) derived from n-eicosane-carboxylic aid, the lignoceryl radical ($C_{24}$) derived from tetracosane-carboxylic acid and the acyl radical ($C_{30}$) derived from triacontane-carboxylic acid. All possible acyl radicals are straight-chain. Apart from the acyl radicals already mentioned having a straight-chain C atom count, those having a non-straight-chain C atom count can also be employed, for example the acyl radical of tridecane-carboxylic acid ($C_3$), the acyl radical of pentadecane-carboxylic acid ($C_5$), the acyl radical of heptadecanecarboxylic acid (margaric acid; $C_{17}$), the acyl radical of heneicosanoic acid ($C_{21}$) and others. Apart from the saturated acyl radicals having a straight-chain or non-straight-chain C atom count, unsaturated acyl radicals are possible, such as oleyl ($C_{18}$), elaidinyl ($C_{18}$), linolyl ($C_{18}$), linolenyl ($C_{18}$) or their homologues having a differing C atom count. Merely for reasons of better availability, acyl radicals having straight-chain C atom counts are preferred.

In the lipid bilayer B of the membrane biosensor according to the invention the two lipid monolayers are with the hydrocarbon radicals of the acyl groups opposite.

Within each lipid monolayer, all acyl groups present therein have essentially the same chain length. This means that in acyl groups of an intended chain length within the abovementioned range for a lipid monolayer those of the following chain lengths with up to 2 C atoms less or more can also be present up to 30 mol %. In the case of an intended chain length of 16 C atoms, those with 14, 15, 17 or 18 C atoms or mixtures thereof can thus be present up to a total of 30 mol%. For reasons of simplified handling, it may be useful and advantageous to incorporate in both lipid monolayers acyl groups of identical chain length. This is also necessary in the preparation processes described above for the formation of the membrane biosensor according to the invention according to (1a) and (2), in which the lipid bilayer organizes itself in order to ensure essentially identical chain lengths in the respective lipid monolayers. The preparation variant (1b), in which specifically only the lower lipid monolayer can initially be prepared, makes it possible, however, to apply the separately applied upper lipid monolayer having acyl groups, which has a different number of C atom counts compared to the lower lipid monolayer. Within the upper lipid monolayer applied, however, all acyl groups in turn have the same chain length.

The spacer C consists of a molecule of ethanolamine which is bonded in an ester-like manner to the phosphate group of the diacylphosphatide. An oligopeptide of 4–20 α-amino acids is then bonded to the N atom of the ethanolamine. Preferably, it is an oligopeptide of 4–10 α-amino acids. The α-amino acids contain 2–10 C atoms, preferably 2–4 C atoms, particularly preferably it is glycine having 2 C atoms. Oligopeptide spacers of such a construction are present in a helical or pleated sheet structure and thereby make possible a high organization in the ratio between the lower monolayer of the lipid bilayer and the support A. This high organization on the one hand makes possible an environment for the receptor D simulating the natural cell membrane and on the other hand avoids contact of this receptor D with the support A. The variability of this spacer in the membrane biosensor according to the invention allows the size and the space requirement of the receptor D to be gone into specifically. The spacer carries finally, with binding to the N atom of the terminal α-amino acid, a reactive group which allows the spaced lower lipid monolayer of the lipid bilayer B to be immobilized on the surface of the corrosion-resistant material with the support A, which allows the sensing of an electrical signal. As has already been shown above, the corrosion-resistant surface of the support A, which allows the sensing of an electrical signal, is a (semi)noble metal, so that a possible reactive group is one of those which, for example, has a thiol or disulfide group. A thiol or disulfide group is possible, in particular, in the case of one of the (semi)noble metals, particularly in the case of gold or in the case of platinum. In the case in which the surface which is corrosion-resistant and allows the sensing of an electrical signal is, for example, doped silicon, a possible reactive group is also one with a silane group.

Such thiol, disulfide or silane groups produce a chemical or physicochemical bonding to the support A. Other reactive groups are: carboxyl groups, isocyanates and acid anhydrides. The construction of the two lipid layers present according to the invention of the lipid bilayer B is readjusted to the naturally occurring phosphatides, sphingomyelins and cholesterol in cell membranes. Phosphatides which occur naturally are those in which two long-chain fatty acids and a phosphoric acid radical (phosphatidic acid) are bonded to the glycerol, a further compound from the group of naturally occurring head groups of phospholipids being bonded to the phosphoric acid radical; such head groups are, for example: choline, glycerol, ethanolamine, serine and inositol. In all cases mentioned, these compounds are amphiphiles; those are preferred which retain the activity of the receptor. In the non-spaced lipid layers, this base is preferably the already-mentioned choline. Other bases-apart from choline are those mentioned above. In the lipid units equipped with a spacer, in the manner described above the ethanolamine and the subsequent further construction of the entire spacer described above including the reactive group initially enters in the position of the choline of the spacers.

Thus there are now available on the support A immobilized lipid bilayers B which, with the aid of the spacer C incorporated in the lower lipid monolayer, have a predeterminable distance from the support A. These lipid bilayers simulate a natural cell membrane. A receptor D can now be incorporated in these lipid bilayers. Such receptors D have a hydrophobic membrane-spanning part with hydrophilic domains of different size. Such receptors can additionally have different lengths. The insertion of these receptors D into the lipid bilayer B takes place spontaneously by self-organization of D in B. By the construction of the lipid bilayer B with acyl radicals of different length and with spacer groups C of different length, the space requirement of receptors D of different length can be considered without such receptors D retaining contact with the support A. By means of the submonolayer initially applied in the preparation process (2), furthermore the specific percentage of lower lipid monolayer can be adjusted which carries a spacer and a reactive group.

Figure 2:
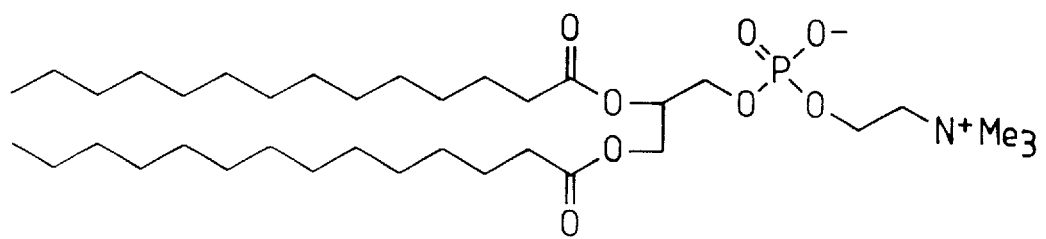
Figure 3:
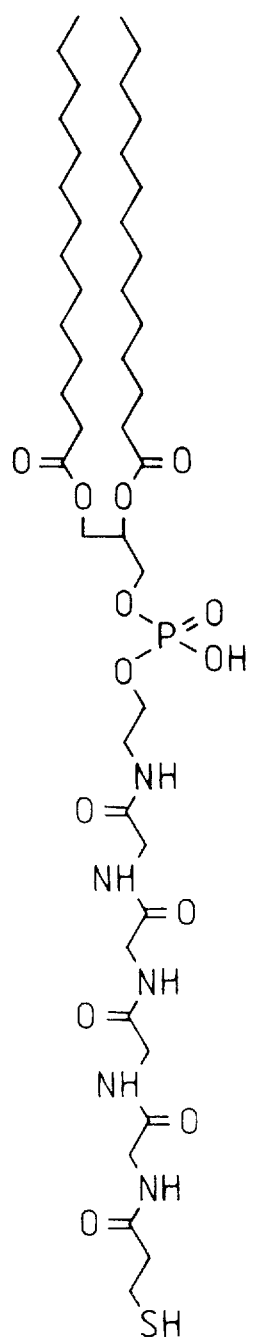
Figure 4A:
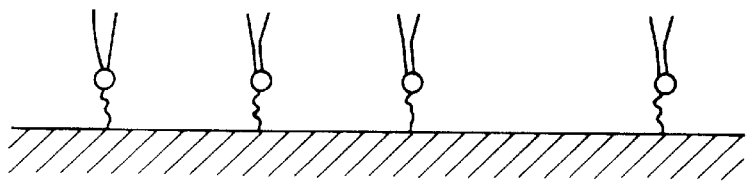
Figure 4B:
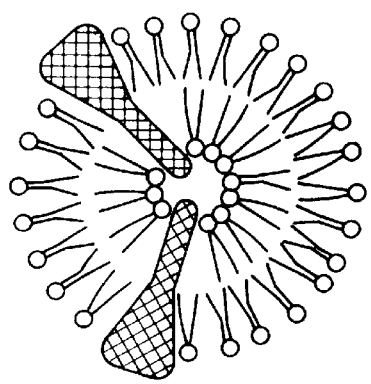
Figure 4B:

The attached FIGS. 1, 2, 3 and 4a to 4c illustrate the construction and a preparation variant of the membrane biosensors according to the invention. In FIG. 1, A is the surface of the solid serving as a support, which consists of a corrosion-resistant material which allows sensing for an electrical signal, B is the lipid bilayer, in the two lipid monolayers with their long-chain hydrocarbon radicals the acyl groups are together, C in a stylized manner is the spacer with which individual lipid molecules of the lower lipid monolayer are bonded to the surface of the support A, and D is an embedded receptor. FIG. 2 shows the construction of non-spaced lipid molecules which arranged from above downwards have the following constituents: two acyl radicals of identical length (in FIG. 1, FIG. 2 and the additionally following FIG. 3 in each case demonstrated as exemplified by the myristyl radical ($C_{14}$)), the glycerol radical, the phosphoric acid radical and the choline radical. FIG. 3 shows the construction of a lipid molecule provided with a spacer C with the radicals arranged from above downwards as follows: two acyl radicals of identical length, the glycerol radical, the phosphoric acid radical, the ethanolamine radical, four glycerol radicals which embody the oligopeptide spacer moiety and the mercaptopropionamide as a reactive group. FIGS. 4a to 4e finally show the stepwise construction of the membrane biosensors according to the invention within the meaning of the preparation variants (3) described above. FIG. 4a in this context shows the application of lipid molecules provided with spacers C, including reactive groups (wavy line represents the entire spacer C, the inner white circle represents the phosphoric acid-glycerol part of the lipid, the two lines starting from the inner white circle represent the two acyl radicals). The arrow pointing from FIG. 4a to FIG. 4b represents the next step, namely the addition of a vesicular solution which is composed of non-spaced phospholipids having an analogous structure to FIG. 4a, but without spacer C and receptors.

Figure 4C:
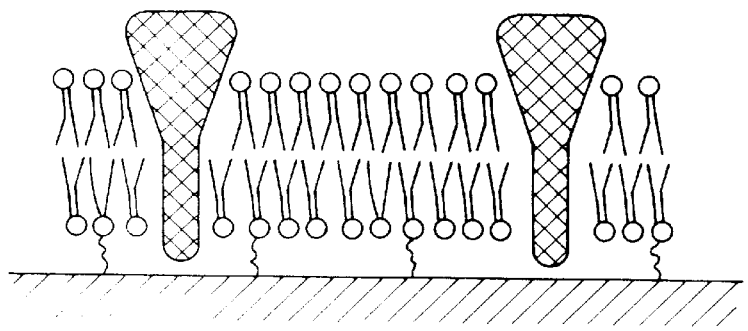

The arrow pointing from FIG. 4b to FIG. 4c then represents the spontaneous self-organization of the lipid bilayer described further above with embedded receptors. It is recognizable that the submonolayer prepared in FIG. 4a is filled up with non-spaced lipid molecules and that the upper lipid monolayer only consists of non-spaced lipid molecules.

EXAMPLES 1.1. Preparation of the gold substrates (solid A as support)

The substrate to be vapor-deposited, inter alia glass or silicon were used, was cleaned in hot 2% strength detergent solution (70° C.) with ultrasound and then rinsed for 20 min with high-purity water in order to remove residual detergent. The substrate was freed from adhering adsorbates in an argon plasma and vapor-deposited in a vapor-deposition unit with a thin chrome layer of about 10–20 nm and then vapor-deposited with a gold layer of 100–200 nm. The electrical sensing took place directly on the gold layer.

1.2. Preparation of the first monolayer

For the preparation of a lipid monolayer consisting of a dimyristyl-phosphatidylethanolamine which carried a spacer of five glycine radicals and a terminal thiol group, the argon plasma-purified gold substrate was incubated with an ethanolic solution containing 0.1–1 mM of this spacer lipid. The self-assembly process was terminated after 1–5 min such that an incomplete lipid monolayer having a degree of coating of approximately 70% was obtained. The coated gold substrate was then rinsed intensively with ethanol.

1.3. Reconstitution of the acetyl choline receptor in vesicles

Starting from isolated membrane fragments of Torpedo marmorata, the nicotinic acetylcholine receptor was reconstituted in vesicles with the aid of the detergent dilution method. Membrane fragments having 1 nmol of α-bungarotoxin binding sites, 5 mg of 1-palmityl-2-oleyl-phosphatidyl-choline and 2% sodium cholate were suspended in a tris buffer and ultrasonicated in an ultrasonic bath until a clear micellar solution was formed. This solution was dialyzed against pure buffer for 12 h.

1.4. Preparation of a lipid bilayer (lipid bilayer B with spacer C) with reconstituted acetylcholine receptor (embedded receptor D)

The vesicles with reconstituted receptor protein obtained from 1.3 were added to the hydrophobic support-immobilized monolayer in a tris buffer and the fusion of the vesicles with the surface was initiated at 30°–40° C. After completion of the fusion process, which as a rule is finished after one to two hours, the vesicle solution was exchanged for pure buffer solution.

What is claimed is:

1. A solid-supported membrane biosensor, consisting of a solid A as a support, a lipid bilayer B as a membrane with spacers C incorporated between A and B and a receptor D embedded in the lipid bilayer, where a) A on the surface facing D consists of a corrosion-resistant material which allows sensing of an electrical signal, b) the lower lipid monolayer of B consists to 1–40% of all lipid molecules of di-($C_8$–$C_{30}$-acyl)-phosphatidyl compounds with a naturally occurring head group and to 60–99% of a di-($C_8$–$_{30}$-acyl)-phosphatide which, however, carries the spacer C instead of the head group, and whose upper lipid monolayer consists to 100% of di-($C_8$–$C_{30}$-acyl)-phosphatidyl compounds with a naturally occurring head group, all acyl groups of a layer essentially being of equal length, but the acyl groups of the lower lipid monolayer being of equal or different length to those of the upper lipid monolayer, c) C consists of 1 molecule of ethanolamine which forms an ester bond to the phosphate group of B, an oligopeptide in helical or pleated sheet structure formed from 4–20 $C_2$–$C_{10}$-α-amino acids and a reactive group which enters into a chemical or physicochemical bond with A, all C of the biosensor being identical, and d) D has no contact with A.

2. A process for the preparation of a membrane biosensor supported by a solid, as claimed in claim 1, which comprises either (1) applying a solution of 1 part of lipid provided with a spacer and $1$–$10^6$ parts of non-spaced lipid in water, an organic solvent from the group consisting of $C_1$–$C_4$-alkanols and $C_3$–$C_6$-ketones or a mixture of several of them to a support A, a lower lipid monolayer, consisting of 60–99% of lipid molecules provided with the spacer and of 1–40% of non-spaced lipid molecules being spontaneously formed, (1a) the upper lipid monolayer additionally also being spontaneously formed from the aqueous solution, or (1b) in a solution not containing water only the lower lipid monolayer being formed, which after a washing process with the organic solvent used is completed to give the lipid bilayer by applying a solution of non-spaced lipid molecules in water, and transferring a micelle solution of a receptor suspension to the lipid bilayer formed according to (1a) or (1b), the receptor D being spontaneously arranged in the lipid bilayer, or (2) transferring a solution of lipid provided with a spacer in one of the above solvents to a support A, after formation of a submonolayer of the lipid removing this solution again from the support, rinsing the submonolayer formed on the support with one of the above solvents and then transferring a micellar solution of water, non-spaced lipid, surfactant and receptor D to the submonolayer, the lipid bilayer being spontaneously completed and the receptor D being spontaneously arranged in the lipid bilayer, or (3) applying a vesicle solution, consisting of receptor molecules and lipids, to the submonolayer formed on the support A, the vesicles spontaneously fusing to the submonolayer and the receptor D spontaneously arranging in the lipid bilayer.

3. The biosensor of claim 1, wherein the lower lipid monolayer of B consists to 10–30% of all lipid molecules of di-($C_8$–$C_{30}$-acyl)-phosphatidyl-choline and to 70–90% of a di-($C_8$–$C_{30}$-acyl)-phosphatide which, however, carries the spacer C instead of the choline.

4. The biosensor of claim 1, wherein the acyl groups contain 10–24 C atoms.

5. The biosensor of claim 1, wherein the α-amino acids employed for the oligopeptide are those having 2–4 C atoms.

6. The biosensor of claim 5, wherein the α-amino acid employed for the oligopeptide is glycine.

7. The biosensor of claim 1, wherein the surface of A facing D consists of gold or platinum.

8. The biosensor of claim 7, wherein the reactive group contains a thiol or disulfide group for entering into a chemical bond with the surface of A consisting of gold or platinum.

* * * * *

UNITED STATES PATENT AND TRADEMARK OFFICE
CERTIFICATE OF CORRECTION

PATENT NO. : 5,846,814
DATED : December 8, 1998
INVENTOR(S) : Galla et al

It is certified that error appears in the above-identified patent and that said Letters Patent is hereby corrected as shown below:

Title Page, [73], "Assignee"   After "Bayer" delete "Aktiengesllschaft" and substitute --Aktiengesellschaft--

Signed and Sealed this

Sixteenth Day of November, 1999

Attest:

Q. TODD DICKINSON

Attesting Officer   Acting Commissioner of Patents and Trademarks